United States Patent
Williams et al.

(10) Patent No.: US 11,291,833 B2
(45) Date of Patent: Apr. 5, 2022

(54) BONDING STRIP FOR FIXING AN ELECTRODE COIL TO A LEAD BODY

(71) Applicant: Medtronic, Inc., Minneapolis, MN (US)

(72) Inventors: Dina L. Williams, Andover, MN (US); Thomas D. Brostrom, Wayzata, MN (US); George W. McFall, Minneapolis, MN (US); Kathryn R. Parsons, Fridley, MN (US); Robert J. Van Drasek, Albertville, MN (US)

(73) Assignee: Medtronic, Inc., Minneapolis, MN (US)

( * ) Notice: Subject to any disclaimer, the term of this patent is extended or adjusted under 35 U.S.C. 154(b) by 649 days.

(21) Appl. No.: 15/975,190

(22) Filed: May 9, 2018

(65) Prior Publication Data

US 2019/0344071 A1    Nov. 14, 2019

(51) Int. Cl.
*A61N 1/05*    (2006.01)
*A61N 1/39*    (2006.01)
*B29C 63/42*   (2006.01)

(52) U.S. Cl.
CPC ......... *A61N 1/0563* (2013.01); *A61N 1/0504* (2013.01); *A61N 1/057* (2013.01); *A61N 1/3918* (2013.01); *B29C 63/42* (2013.01)

(58) Field of Classification Search
CPC .......... A61N 1/05; A61N 1/39; A61N 1/0563; A61N 1/3918; A61N 1/3956; A61N 1/3906; A61N 1/39622; A61N 1/3962; A61N 1/3752; A61N 1/375; A61N 1/3968; A61N 1/3975

USPC ......................................... 607/119, 125, 127
See application file for complete search history.

(56) References Cited

U.S. PATENT DOCUMENTS

| | | | |
|---|---|---|---|
| 4,860,769 A | 8/1989 | Fogarty et al. | |
| 4,934,049 A | 6/1990 | Kiekhafer et al. | |
| 5,042,143 A | 8/1991 | Holleman et al. | |
| 5,105,826 A | 4/1992 | Smits et al. | |
| 5,144,960 A * | 9/1992 | Mehra .................. | A61N 1/0563 607/125 |
| 5,342,407 A | 8/1994 | Dahl et al. | |

(Continued)

OTHER PUBLICATIONS (PCT/US2019/031081) PCT Notification of Transmittal of the International Search Report and the Written Opinion of the International Searching Authority, dated Aug. 7, 2019, 11 pages.

(Continued)

*Primary Examiner* — Jon Eric C Morales
(74) *Attorney, Agent, or Firm* — Shumaker & Sieffert, P.A.

(57) ABSTRACT

The disclosure describes a medical electrical lead including bonding strip to bond an elongate electrode coil to an elongate lead body to reduce damage to the medical electrical lead during manipulation of the medical electrical lead. The elongate lead body extends from a proximal end to a distal end and includes a proximal portion and a distal portion. The elongate electrode coil surrounds at least part of the distal portion of the elongate lead body. The bonding strip extends axially along the elongate electrode coil and extends only partially around the circumference of the elongate electrode coil for at least part of the length of the bonding strip, where at least a portion of the bonding strip is bonded to the elongate lead body to fix a portion of the elongate electrode coil to the elongate lead body.

30 Claims, 7 Drawing Sheets

(56) References Cited

U.S. PATENT DOCUMENTS

| | | | |
|---|---|---|---|
| 5,347,708 A | | 9/1994 | Bischoff et al. |
| 5,387,233 A | | 2/1995 | Alferness et al. |
| 5,439,485 A | * | 8/1995 | Mar .................... A61N 1/0563 607/119 |
| 5,555,618 A | | 9/1996 | Winkler |
| 5,660,892 A | | 8/1997 | Robbins et al. |
| 5,925,073 A | | 7/1999 | Chastain et al. |
| 7,313,444 B2 | | 12/2007 | Pianca et al. |
| 7,512,447 B2 | | 3/2009 | Marshall et al. |
| 7,684,864 B2 | | 3/2010 | Olson et al. |
| 8,437,864 B2 | | 5/2013 | Siefert |
| 8,498,721 B2 | | 7/2013 | Scheiner et al. |
| 2003/0105501 A1 | | 6/2003 | Warman et al. |
| 2006/0241734 A1 | | 10/2006 | Marshall et al. |
| 2006/0247753 A1 | | 11/2006 | Wenger et al. |
| 2007/0270928 A1 | * | 11/2007 | Erlebacher .......... A61N 1/0563 607/126 |
| 2010/0121421 A1 | | 5/2010 | Duncan et al. |
| 2010/0125321 A1 | | 5/2010 | Lynn et al. |
| 2011/0301680 A1 | | 12/2011 | Boser et al. |
| 2012/0029335 A1 | | 2/2012 | Sudam et al. |
| 2013/0030511 A1 | * | 1/2013 | Bardy ................. A61N 1/3956 607/119 |
| 2013/0338730 A1 | | 12/2013 | Shiroff et al. |
| 2015/0306374 A1 | | 10/2015 | Seifert et al. |
| 2016/0158567 A1 | | 6/2016 | Marshall et al. |

OTHER PUBLICATIONS

Baudoin, Y. P., et al., "The superior epigastric artery does not pass through Larrey's space (trigonum sternocostale)," Surg.Radiol. Anat. 25.3-4; Aug. 2003: 259-62.

* cited by examiner

BONDING STRIP FOR FIXING AN ELECTRODE COIL TO A LEAD BODY

TECHNICAL FIELD

The present application relates to electrical stimulation leads and, more particularly, medical electrical leads including an elongate electrode coil.

BACKGROUND

Medical electrical leads may be used to sense physiological parameters, such as cardiac function, or deliver stimulation therapy to a patient. For example, malignant tachyarrhythmia, such as ventricular fibrillation, is an uncoordinated contraction of the cardiac muscle of the ventricles in the heart. If this arrhythmia continues for more than a few seconds, it may result in cardiogenic shock, cessation of effective blood circulation, and, in some instances, sudden cardiac death (SCD). In patients at high risk of ventricular fibrillation, the use of an implantable cardioverter-defibrillator (ICD) system has been shown to be beneficial at reducing occurrences of SCD. An IMD system may include an ICD, which is a battery powered electrical stimulation device that is coupled to one or more medical electrical leads placed within or near the heart. If the ICD detects an arrhythmia, the ICD may send defibrillation electrical stimulation via the medical electrical leads to stimulate the heart and restore its normal rhythm. Other applications of medical electrical leads include, for example, neurostimulation and neuromuscular stimulation.

SUMMARY

A medical electrical lead may include an elongate electrode coil including a plurality of turns of at least one filar surrounding an elongate lead body. The elongate electrode coil may be bonded or otherwise affixed with a bonding strip to the elongate lead body along only a portion of its circumference such that each respective turn of the plurality of turns of the filar may be fixed relative to adjacent turns of the plurality of turns of the filar and the elongate lead body. Fixing the elongate electrode coil to the elongate lead body with a bonding strip may reduce damage to the medical electrical lead during manipulation of the medical electrical lead, such as during an implantation procedure.

In some examples, the disclosure describes a medical electrical lead that includes an elongate lead body, an elongate electrode coil, and a bonding strip. The elongate lead body extends from a proximal end to a distal end and includes a proximal portion and a distal portion. The elongate electrode coil surrounds at least part of the distal portion of the elongate lead body. The bonding strip extends axially along the elongate electrode coil and extends only partially around a circumference of the elongate electrode coil for at least part of a length of the bonding strip. At least a portion of the bonding strip is bonded to the elongate lead body to fix a portion of the elongate electrode coil to the elongate lead body.

In some examples, the disclosure describes a method of implanting a medical electrical lead that includes an elongate lead body extending from a proximal end to a distal end and includes a proximal portion and a distal portion, an elongate electrode coil surrounding at least part of the distal portion of the elongate lead body, and a bonding strip extending axially along the elongate electrode coil and extending only partially around a circumference of the elongate electrode coil for at least part of a length of the bonding strip, where at least a portion of the bonding strip is bonded to the elongate lead body to fix a portion of the elongate electrode coil to the elongate lead body. The method includes creating an incision at a first location proximate a center of a torso of a patient. The method also includes introducing an implant tool into the patient through the incision at the first location. The method also includes advancing a distal end of the implant tool through a substernal space underneath the sternum to create a substernal tunnel. The method also includes introducing the medical electrical lead into the substernal tunnel such that the distal portion of the elongate lead body is positioned between a first position proximate to the xiphoid process and a second position superior to the xiphoid process such that the elongate electrode coil is positioned anterior to a right ventricle of the heart and the bonding strip is positioned anterior to the elongate electrode coil.

In some examples, the disclosure describes a method of forming a medical electrical lead that includes positioning an elongate electrode coil to surround at least part of a distal portion of an elongate lead body extending from a proximal end to a distal end. The method also includes disposing a bonding strip axially along the elongate electrode coil and only partially around the circumference of the elongate electrode coil for at least part of the length of the bonding strip. The method also includes applying pressure and heat to at least a portion of the bonding strip to bond the portion of the bonding strip to the elongate lead body to fix a portion of the elongate electrode coil to the elongate lead body.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

Figure 1A:
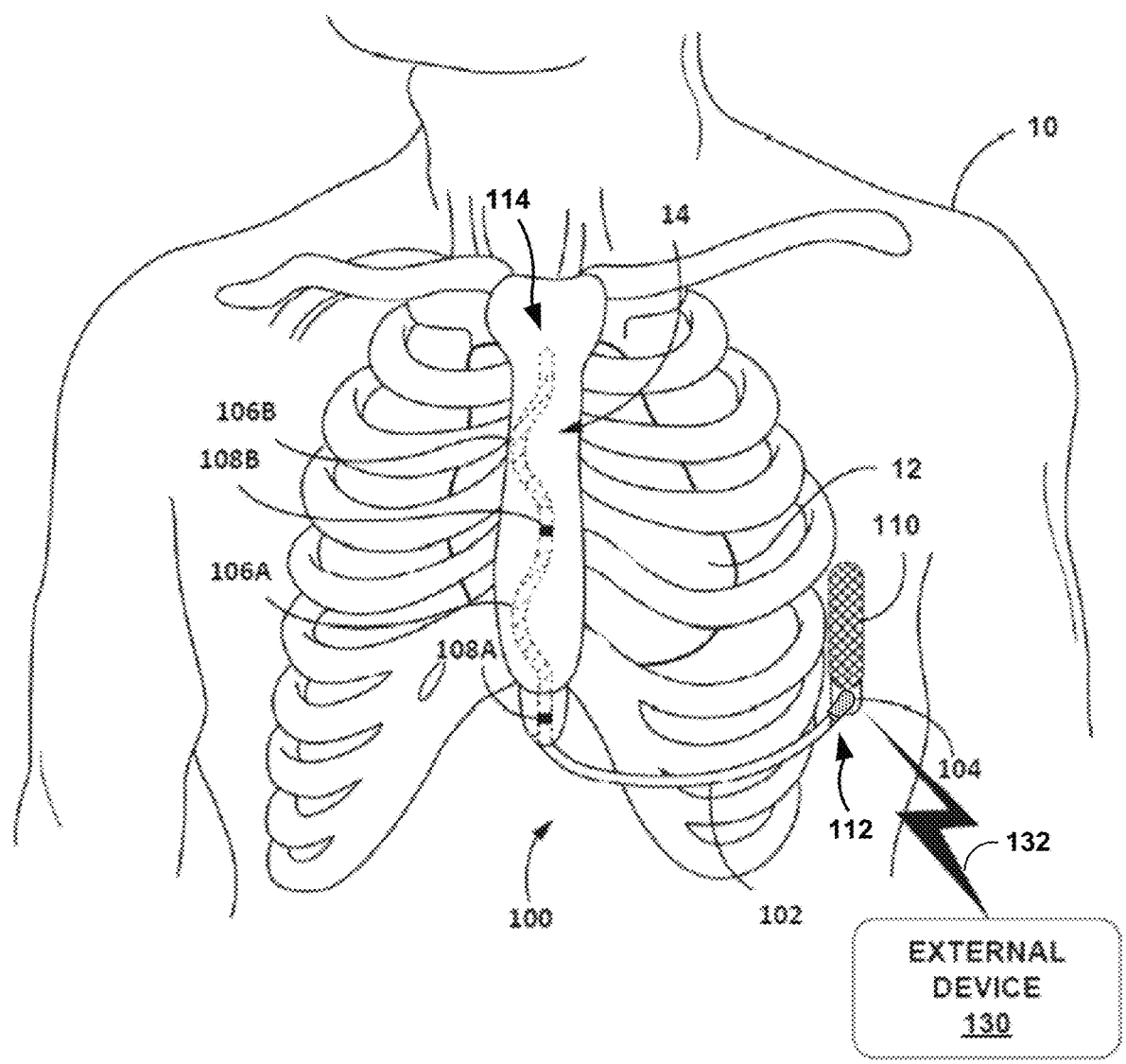
FIGS. 1A-1C are conceptual and schematic diagrams illustrating a front-view, a side-view, and a top-view, respectively, of an example medical device system including a medical electrical lead in a patient.

The details of one or more examples of this disclosure are set forth in the accompanying drawings and the description below. Other features, objects, and advantages of this disclosure will be apparent from the description and drawings, and from the claims.

DETAILED DESCRIPTION

The disclosure describes a medical electrical lead including a bonding strip to fix an elongate electrode coil to an elongate lead body and methods for implanting and forming such leads. A medical electrical lead may include an elongate electrode coil surrounding an elongate lead body. The elongate electrode coil includes a plurality of turns of at least one filar (e.g., a conductive metal wire). The medical electrical lead also includes a bonding strip that fixes the elongate electrode coil to the elongate lead body. The bonding strip may extend axially along the elongate electrode coil and extend only partially around the circumference of the elongate electrode coil for at least part of the length of the elongate electrode coil. At least a portion of the bonding strip may be bonded to the elongate lead body. For example, a plurality of portions of the bonding strip disposed between each respective turn of the plurality of turns of the filar may be bonded to the elongate lead body.

By extending axially along the elongate electrode coil, the bonding strip may reduce movement of one or more turns of the plurality of turns of the filar relative to other turns of the filar while allowing some relative movement. For example, a respective turn of the plurality of turns may move by bending, compressing, or twisting during implantation of the medical electrical lead into an extracardiovascular (e.g., subcutaneous or a substernal) or intravenous portion of a patient. As the bonding strip does not fix the entirety of each turn of the filar to the elongate lead body, the bonding strip may allow some relative movement between the respective turns of the filar, while constraining movement to reduce damage to the medical electrical lead due to excessive movement of the turns relative to each other.

The bonding strip may also enable control of the amount of exposed surface area of the elongate electrode coil by selecting a length, a width, and a thickness of the bonding strip. In some examples, the amount of exposed surface area of the elongate electrode coil may be selected to affect the conductance of the elongate electrode coil, to control the directivity of the electrical stimulation (e.g., defibrillation stimulation, pacing stimulation, such as antitachycardia pacing, bradycardia pacing, and/or post-shock pacing, or the like) delivered using the elongate electrode coil, or both. In some examples, the position of exposed surface area of the elongate electrode coil relative to the anatomy of the patient may be controlled to substantially align the exposed surface area of the elongate electrode relative to the target tissue (e.g., the heart) to control the directionality of the electrical stimulation therapy relative to the medical electrical lead. In this way, the bonding strip may be configured to affect the electrical stimulation therapy delivered using the medical electrical lead. In some examples, the medical electrical lead may be an implantable defibrillation lead, and the elongate electrode coil may be an elongate defibrillation electrode coil.

Figure 1B:
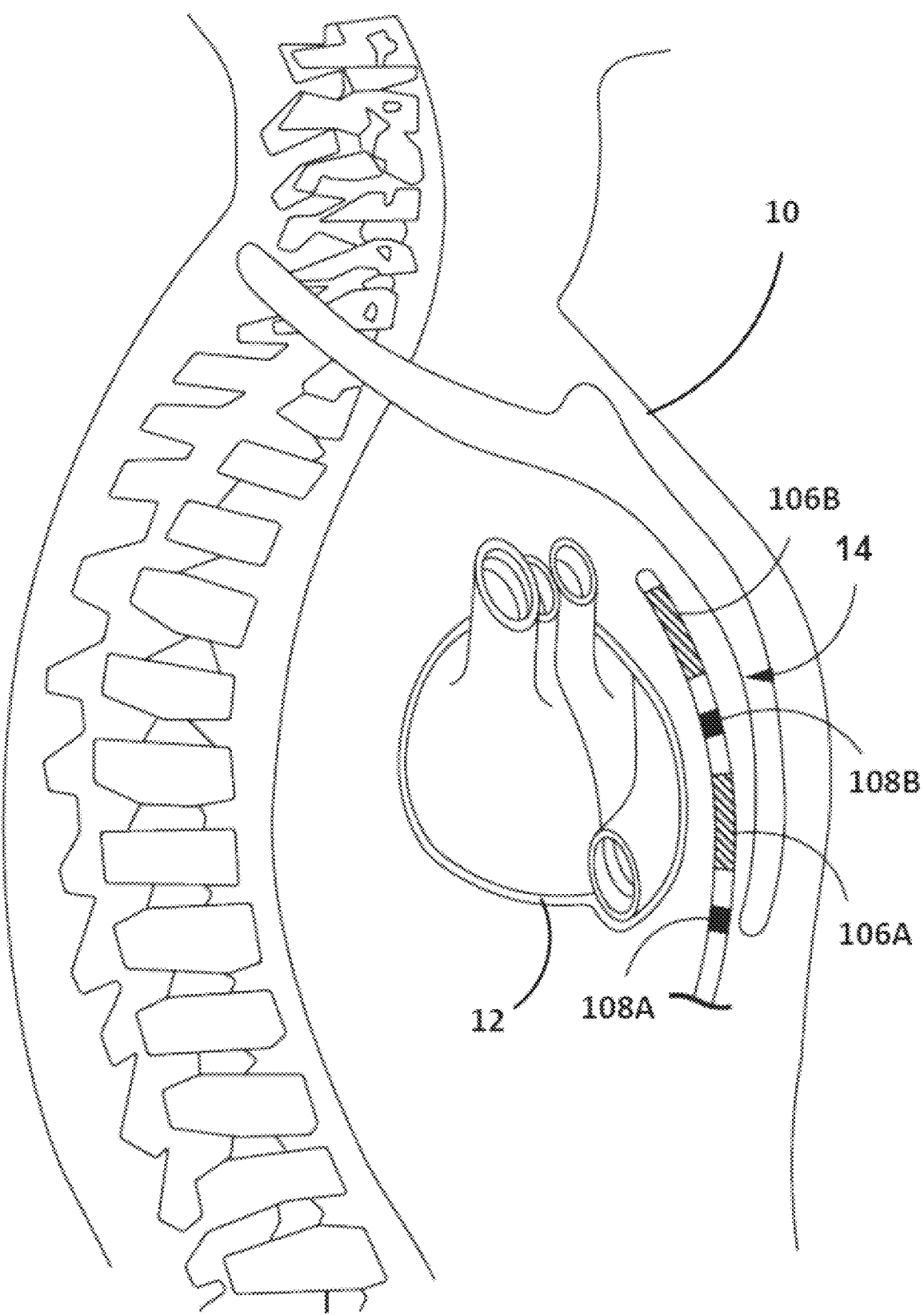
Figure 1C:
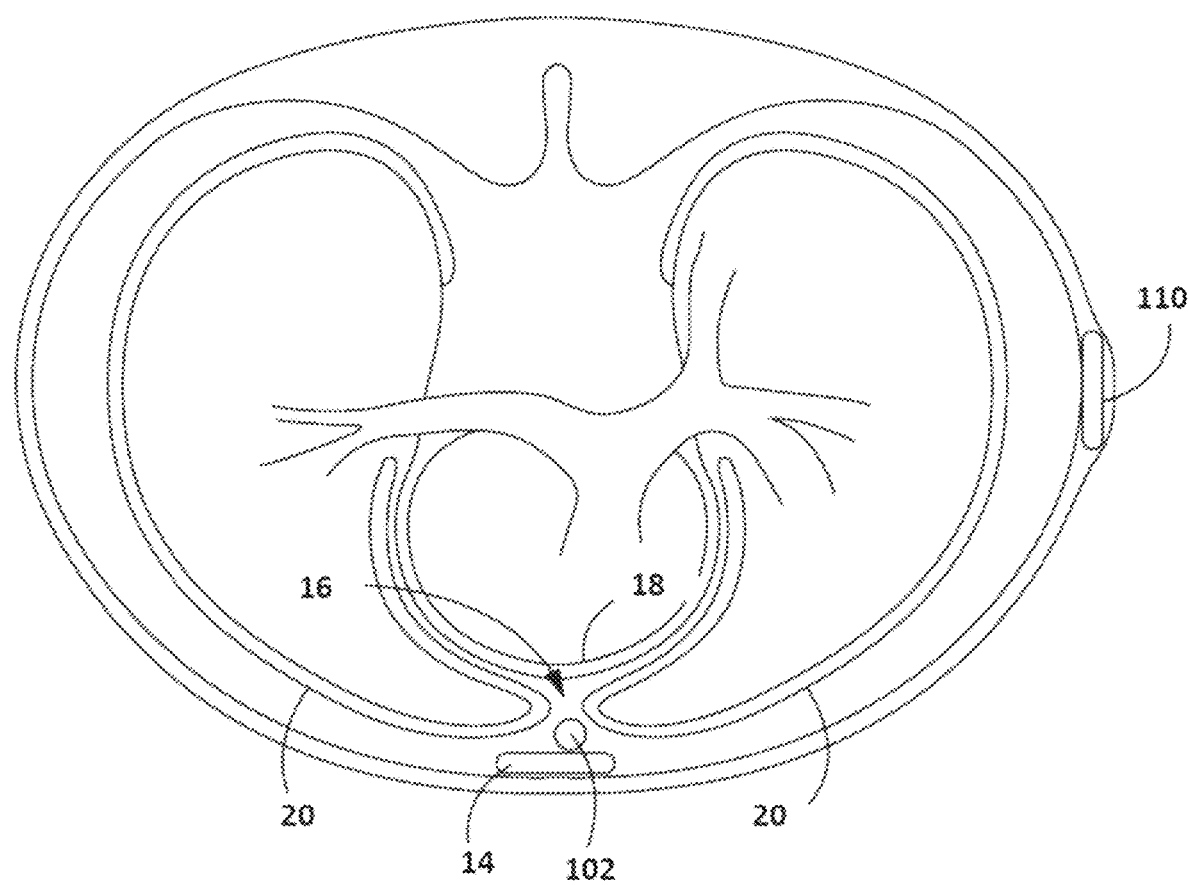

FIGS. 1A-1C are conceptual and schematic diagrams illustrating a front-view, a side-view, and a top-view, respectively, of an example implantable medical device (IMD) system 100 including a medical electrical lead 102 implanted in a patient 10. In the illustrated examples, IMD system 100 is an extracardiovascular IMD system implanted within patient 10. IMD system 100 may not be limited to treatment of a human patient. In alternative examples, IMD system 100 may be implemented in non-human patients, such as primates, canines, equines, pigs, bovines, ovines, and felines. These other animals may undergo clinical or research therapies that may benefit from the subject matter of this disclosure.

In general, IMD system 100 may include one or more medical devices, electrical leads, external devices, or other components that include the medical electrical leads described herein. As shown in FIG. 1A, IMD system 100 includes an implantable cardioverter-defibrillator (ICD) 110. In some examples, IMD system 100 may include other medical devices such as other neuromuscular stimulator devices, neurostimulator devices, or the like. In some examples, ICD 110 may include a housing electrode formed on or by the housing of ICD 110. ICD 110 is connected to at least one medical electrical lead, such as implantable medical electrical lead 102. In some examples, ICD 110 may be connected to two or more implantable medical electrical leads 102.

Implantable medical electrical lead 102 includes an elongate lead body extending from a proximal end 112 to a distal end 114. Proximal end 112 may include a connector 104 configured to be connected to ICD 110. A distal portion of implantable medical electrical lead 102 includes one or more electrodes that include an elongate electrode coil. As shown in FIG. 1A, implantable medical electrical lead 102 includes defibrillation electrodes 106A and a 106B (collectively, "defibrillation electrodes 106"). For example, defibrillation electrodes 106 may be positioned on the distal portion of the elongate lead body that extends along the sternum 14. In some examples, the distal portion of implantable medical electrical lead 102 may include fewer or more defibrillation electrodes 106. In some examples, the distal portion of implantable medical electrical lead 102 may also include sensing and/or pacing electrodes 108A and 108B (collectively, "sensing and/or pacing electrodes 108"). Sensing and/or pacing electrodes 108 may be positioned distal to one or more defibrillation electrode of defibrillation electrodes 106, proximal to one or more defibrillation electrode of defibrillation electrodes 106, or both (e.g., one sensing electrode or sensing electrode pair proximal to defibrillation electrodes 106 and one sensing electrode or sensing electrode pair distal to defibrillation electrodes 106). In some examples, the distal portion of implantable medical electrical lead 102 may include fewer or more sensing and/or pacing electrodes 108. In some examples, defibrillation electrodes 106 may be configured to both sense electrical physiological signals and deliver electrical stimulation therapy. In some examples, one or both of sensing and/or pacing electrodes may include elongate electrode coils and be fixed to the elongate lead body using a bonding strip in accordance with this disclosure.

Implantable medical electrical lead 102 may have a generally uniform cross-sectional shape, such as, for example, a generally tubular or cylindrical shape. In other examples, implantable medical electrical lead 102 may include a flat, ribbon, or paddle shape along at least a portion of the length of implantable medical electrical lead 102. In examples in which implantable medical electrical lead 102 includes a flat, ribbon, or paddle shape, the width of implantable medical electrical lead 102 may be between 1 millimeter and 3.5 millimeters. In some examples, implantable medical electrical lead 102 may define a diameter of about 3 French (Fr) to about 9 Fr. In other examples, implantable medical electrical lead 102 may be less than 3 Fr and more than 9 Fr. Other medical electrical lead designs may be used without departing from the scope of this application.

The elongate lead body of implantable medical electrical lead 102 may be formed from a nonconductive material. In some examples, the elongate lead body may include a thermoplastic, such as, for example, a polyurethane based polymer, a fluoropolymer, mixtures thereof, and other appropriate materials. The elongate lead body may include at least one lumen. Each respective lumen of the at least one lumen may include at least one conductor, such as, for example, four lumens each including a respective conductor. The at least one conductor may include any suitable electrically conductive material, such as, for example, MP35N nickel-cobalt alloy. In some examples, the at least one conductor include an electrically insulative jacket, such as ethylene tetrafluoroethylene, polytetrafluoroethylene, or the like, disposed around the conductor and within the respective lumen. In some examples, the at least one conductor may include a coaxial conductor. Each respective conductor of the at least one conductors may electrically couple a respective electrode (e.g., defibrillation electrodes 106) to ICD 110.

Defibrillation electrodes 106 include an elongate electrode coil configured to deliver electrical stimulation therapy to patient 10, e.g., a cardioversion pulse or a defibrillation pulse. The elongate electrode coil may include any suitable electrically conductive material. In some examples, the elongate electrode coil may include a substrate (e.g., wire), such as tantalum. In some examples, the elongate electrode coil substrate may include a coating, such as a platinum iridium coating. In some examples, the elongate electrode coil may include a single filar coil. In other examples, the elongate electrode coil may include a multi-filar coil, such as a bifilar coil.

Implantable medical electrical lead 102 may be configured in different sizes and shapes, such as may be appropriate for intended purposes, e.g., for different patients or for different therapies. In some examples, the distal portion of implantable medical electrical lead 102 including defibrillation electrodes 106 may have one or more curved sections, such as a serpentine shape. In some examples, the distal portion of implantable medical electrical lead 102 may be straight (e.g., straight or nearly straight). In other examples, the distal portion of implantable medical electrical lead 102 may include branches, biased portions expanding away from a central shaft, or other shapes (e.g., with one or more electrodes disposed on the branches, shaft, or biased portions).

As shown in FIGS. 1A-1C, ICD 110 may be implanted subcutaneously or submuscularly on the left side of patient 10, above the ribcage, and implantable medical electrical lead 102 may be implanted at least partially in a substernal space, e.g., between the ribcage or sternum 14 and heart 12. Generally, "substernal space" may refer to the region defined by the undersurface between sternum 14 and the body cavity but not including pericardium 18. For example, the substernal space may include the region posterior to the sternum 14 and anterior to the ascending aorta. The substernal space may alternatively be referred to by the terms "retrosternal space" or "mediastinum" or "infrasternal" as is known to those skilled in the art and includes the region referred to as the anterior mediastinum. In some examples, implantable medical electrical lead 102 may be placed below or along sternum 14 such that a therapy vector between defibrillation electrodes 106 and a housing electrode formed by or on ICD 110 (or a second electrode on the same or different implantable medical electrical lead) is substantially across a ventricle of heart 12. For example, the therapy vector may be viewed as a line that extends from a point on each respective defibrillation electrode of defibrillation electrodes 106 (e.g., a center of each respective defibrillation electrode of defibrillation electrodes 106 relative to the longitudinal axis of each respective defibrillation electrode of defibrillation electrodes 106) to a point on the housing electrode of ICD 110 (or a second electrode on the same or different implantable medical electrical lead).

In some examples, a proximal portion of implantable medical electrical lead 102 extends subcutaneously from ICD 110 toward sternum 14 and a distal portion of implantable medical electrical lead 102 extends superior under or below sternum 14 in the anterior mediastinum 16 (FIG. 1C). The anterior mediastinum 16 is bounded laterally by the pleurae 20 (FIG. 1C), posteriorly by the pericardium 18 (FIG. 1C), and anteriorly by the sternum 14. In some examples, the anterior wall of the anterior mediastinum may also be formed by the transversus thoracics and one or more costal cartilages. The anterior mediastinum includes loose connective tissue (such as areolar tissue), lymph vessels, lymph glands, substernal musculature (e.g., transverse thoracic muscle), branches of the internal thoracic artery, and the internal thoracic vein. In some examples, the distal portion of implantable medical electrical lead 102 extends along the posterior side of the sternum 14 substantially within the loose connective tissue or substernal musculature of the anterior mediastinum.

In some examples, implantable medical electrical lead 102 may be at least partially implanted in other intrathoracic locations, such as other non-vascular, extra-pericardial locations, including the gap, tissue, or other anatomical features around the perimeter of and adjacent to, but not attached to, pericardium 18 or other portion of the heart and not above the sternum 14 or ribcage. The term "extra-pericardial" space may refer to a region around the outer heart surface, but not within pericardium 18. The region defined as the extra-pericardial space includes the gap, tissue, bone, or other anatomical features around the perimeter of, and adjacent to the pericardium. In some examples, implantable medical electrical lead 102 may be at least partially implanted within pericardium 18, e.g., between the pericardial sac and heart 12. In some examples, implantable medical electrical lead 102 may be implanted at transvenous locations. In some examples, implantable medical electrical lead 102 may be implanted at other extracardiovascular locations. In some examples, implantable medical electrical lead 102 may extend subcutaneously above the ribcage from ICD 110 toward a center of the torso (e.g., proximate to the xiphoid process) of patient 10, bend or turn near the center of the torso, and extend subcutaneously superior above the ribcage or sternum 14. In some examples, implantable medical electrical lead 102 may be offset laterally to the left or the right of the sternum 14 or located over the sternum 14. In some examples, implantable medical electrical lead 102 may extend substantially parallel to the sternum 14 or be angled lateral from the sternum 14 at either the proximal or distal end.

Implantable medical electrical lead 102 and/or ICD 110 may be implanted into patient 10 using, for example, delivery systems (e.g., a tunneling tool and/or a sheath) or other devices that may be inserted into a patient (e.g., the substernal space of the patient). The delivery system may include an implant tool. The implant tool, in one example, may define a channel configured to receive a medical lead, for implanting the medical lead into the substernal space. In another example, the implant tool comprises an elongate tunneling tool and a sheath. In some examples, the implant tool comprises one or more electrodes, such as on the elongate tunneling tool, the sheath, or both, for positioning the implantable medical electrical lead 102. By using the systems and techniques described herein with the delivery system, the implantable medical electrical lead 102 may be placed such that a therapy vector between defibrillation electrode 106 and housing 110 (or a can electrode) is substantially across a ventricle of heart 12. In some examples, implantable medical electrical lead 102 may be implanted substantially centered under sternum 14. In other examples, implantable medical electrical lead 102 may be implanted such that it is offset laterally from the center of sternum 14.

ICD 110 may be configured to deliver high-energy cardioversion or defibrillation stimulation to heart 12 of patient 10. The high-energy cardioversion or defibrillation stimulation may be delivered when atrial or ventricular tachyarrhythmias (e.g., atrial fibrillation or ventricular fibrillation) is detected (e.g., sensed) in heart 12. In some examples, cardioversion electrical stimulation may be delivered in synchrony with a detected R-wave when tachyarrhythmias detection criteria are met. In other examples, when the R-wave cannot be discerned from signals sensed by ICD 110, defibrillation electrical stimulation may be delivered when tachyarrhythmias criteria are met.

For example, ICD 110 may sense cardiac electrical signals via one or more sensing vectors to detect atrial or ventricular tachyarrhythmias. In some examples, the one or more sensing vectors may include a vector extending from defibrillation electrodes 106 to the housing electrode of ICD 110. In some examples, the one or more sensing vectors may include a vector extending from one or more sensing and/or pacing electrodes 108 to the housing electrode of ICD 110, defibrillation electrodes 106, and/or a different sensing electrode. The sensed electrical signals may include electrical signals generated by cardiac muscle and indicative of depolarizations and repolarizations of heart 12 at various times during the cardiac cycle. In some examples, processing circuitry of ICD 110 may analyze first electrical signals sensed by the one or more sensing vectors to detect tachyarrhythmia, such as ventricular tachycardia or ventricular fibrillation. In response to detecting the tachyarrhythmia, ICD 110 may begin to charge a storage element, such as a bank of one or more capacitors. When charged, processing circuitry of ICD 110 may analyze second electrical signals sensed by the one or more sensing vectors to determine that tachyarrhythmia is still present. In response to determining that tachyarrhythmia is still present, ICD 110 may deliver one or more defibrillation pulses to heart 12 via electrode 106. Additionally or alternatively, ICD 110 may deliver pacing therapy, such as between one or more of defibrillation electrodes 106, sensing and/or pacing electrodes 108, and the housing electrode of ICD 110. In some examples, the electrical stimulation therapy may include antitachycardia pacing (ATP).

In some examples, IMD 100 may be communicatively coupled to an external device 130 via link 132. For example, external device 130 include processing circuitry configured to control an operation of ICD 110. Link 132 may include any suitable wired or wireless connection. In some examples, the processing circuitry of external device 130 may be configured to detect an R-wave based on one or more indications received from ICD 110 and/or control ICD 110 to deliver one or more electrical stimulation therapies. In some examples, the processing circuitry of external device 130 may be configured to determine whether tachyarrhythmias criteria are met based on one or more indications received from ICD 110 and/or control ICD 110 to deliver one or more cardioversion electrical stimulations. In this way, external device 130 may control one or more operations of IMD 100. In some examples, external device 130 may be a computing device, e.g., used in a home, ambulatory, clinic, or hospital setting, to communicate with ICD 110 via wireless telemetry. External device 130 may include communication circuitry configured to communicate with ICD 110. For example, communication techniques used by ICD 110 and external device 130 include radiofrequency (RF) telemetry, which may be an RF link established via Bluetooth, WiFi, or medical implant communication service (MICS). In some examples, the communication may include one-way communication in which one device is configured to transmit communication messages and the other device is configured to receive those messages. In some examples, the communication may instead include two-way communication in which each device is configured to transmit and receive communication messages. In this way, external device 130 may be used to program commands or operating parameters into ICD 110 for controlling its functioning, such as when configured as a programmer for ICD 110. In some examples, external device 130 may retrieve data from ICD 110, including device operational data. In some examples, external device 130 may be a programmer, external monitor, or consumer device, such as a smartphone. In some examples, external device 130 may be coupled to a remote patient monitoring system, such as Carelink®, available from Medtronic plc, of Dublin, Ireland. In some examples, a user may program or update, via external device 130, parameters that define an electrical stimulation therapy. The user may include patient 10, a physician, technician, surgeon, electrophysiologist, or other healthcare professional.

In some examples, implantable medical electrical lead 102 may include one or more bonding strips extending axially along defibrillation electrodes 106. A bonding strip may extend only partially around the circumference of a respective defibrillation electrode of defibrillation electrodes 106 for a majority of the length of the bonding strip. At least a portion of the bonding strip may be bonded to the elongate lead body of implantable medical electrical lead 102. By bonding to the elongate lead body, the bonding strip may fix a portion of a respective defibrillation electrode of defibrillation electrodes 106 to the elongate lead body.

FIGS. 2A, 2B, 2C, and 2D are conceptual and schematic diagrams illustrating a portion of an example implantable medical electrical lead 200 including bonding strips 202A and 202B (collectively, "bonding strips 202") and an integrally formed collar 218. Implantable medical electrical lead 200 may be an example of implantable medical electrical lead 102 of FIG. 1. As described above, in other examples, the lead need not be implantable, for example, the lead may be used externally to a patient or may be insertable but not implantable in a patient. Further, although the example of FIGS. 2A-2D is described as a defibrillation lead and defibrillation electrode, in other examples, similar principles may be applied to other types of leads and electrodes, e.g., any type of elongate electrode coil.

Figure 2A:
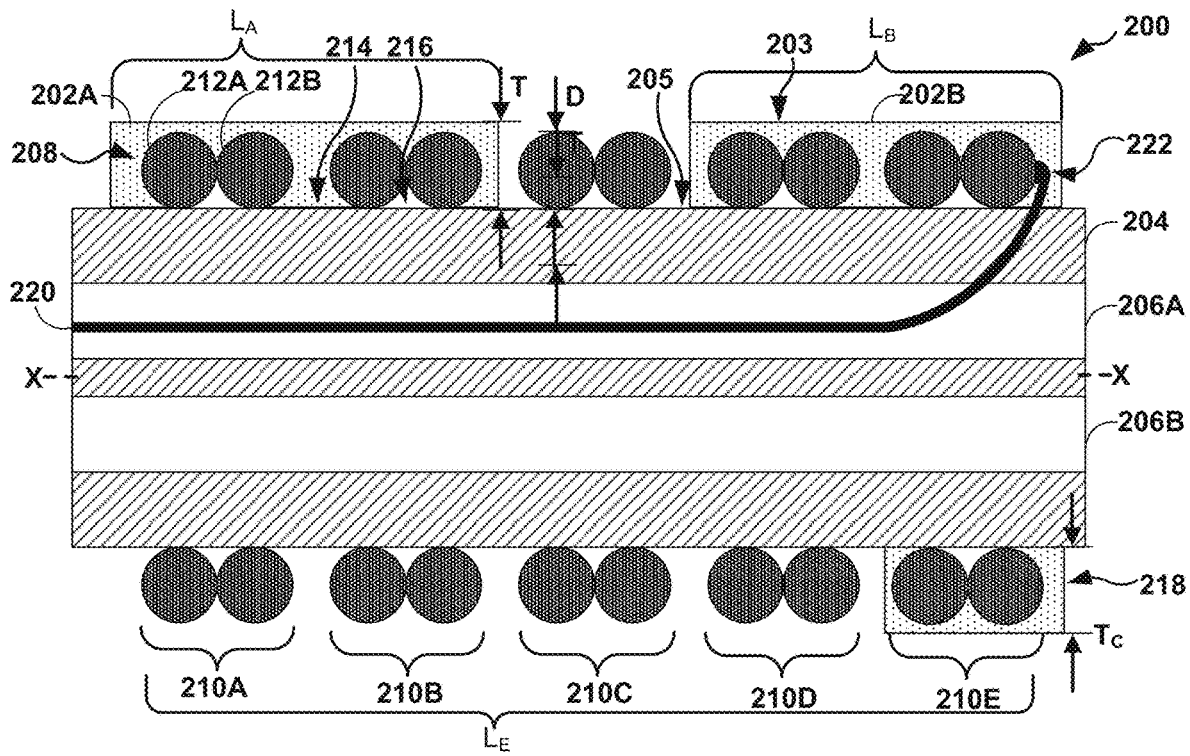
FIGS. 2A-2D are conceptual and schematic diagrams illustrating a portion of an example medical electrical lead including a bonding strip and an integrally formed collar.
Figure 2B:
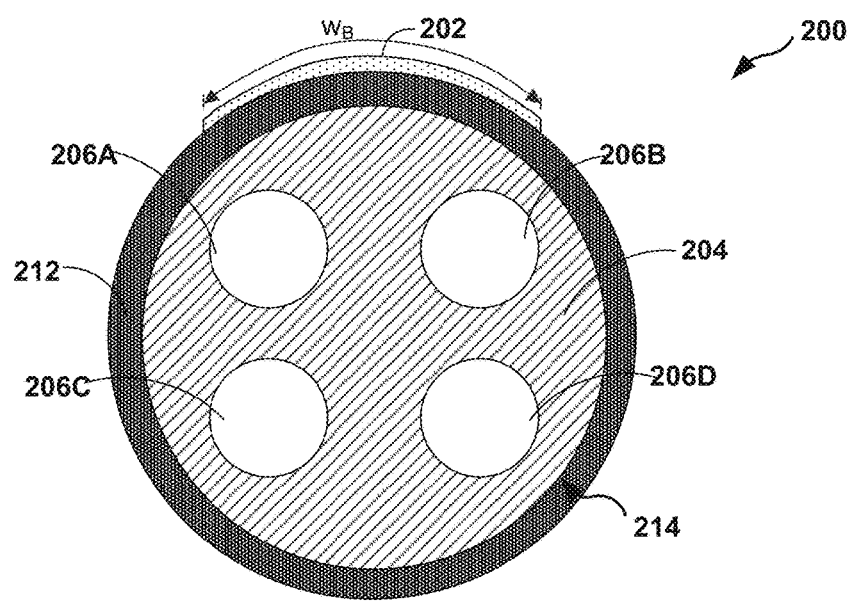
Figure 2C:
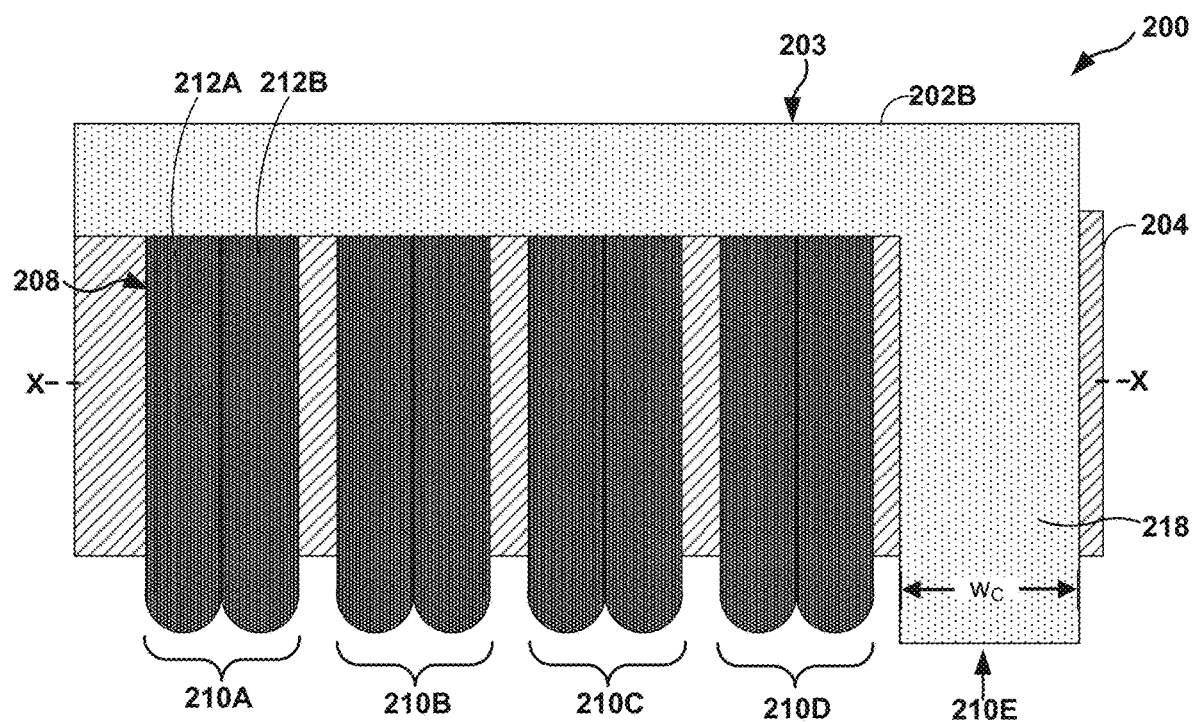
Figure 2D:
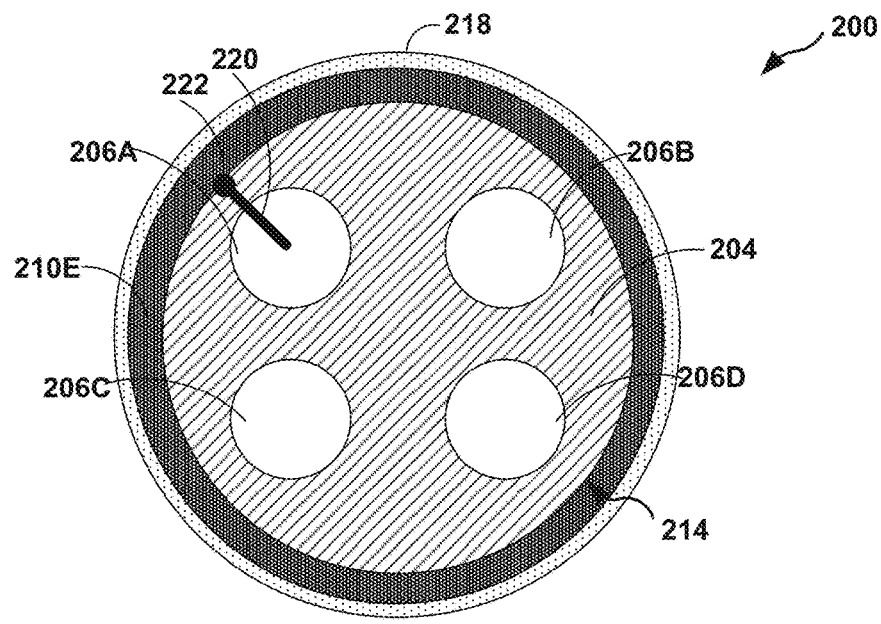

FIGS. 2A and 2B are a longitudinal cross section and a radial cross section, respectively, of implantable medical electrical lead 200 including bonding strips 202. FIGS. 2C and 2D are a longitudinal sideview and a radial cross section, respectively, of implantable medical electrical lead 200 including bonding strips 202B and integrally formed collar 218. Implantable medical electrical lead 200 may be the same as or substantially similar to implantable medical electrical lead 102 as discussed above with respect to FIGS. 1A to 1C. For example, implantable medical electrical lead 200 includes an elongate lead body 204 defining an axis (e.g., the X-X axis shown in FIGS. 2A and 2C) and extending from a proximal end to a distal end and defining surface 205. Elongate lead body 204 may define lumens 206A, 206B, 206C, and 206D (collectively, "lumens 206"). In other examples, elongate lead body 204 may define fewer or more lumens. As discussed above with respect to FIG. 1, one or more of respective lumens may include one or more respective conductors that electrically couple the defibrillation electrode (e.g., elongate electrodes 106) to the ICD (e.g., ICD 110). For example, lumen 206A includes conductor 220 that electrically couples defibrillation electrode 208 to an ICD. Defibrillation electrode 208 includes bifilar defibrillation electrode coil filars 212A and 212B (collectively, "defibrillation electrode coil 212"). In other examples, defibrillation electrode may include more or fewer filars. Defibrillation electrode coil 212 may define a plurality of turns 210A, 210B, 210C, 210D, and 210E (collectively, "plurality of turns 210").

As shown in FIGS. 2A-2C, implantable medical electrical lead 200 includes bonding strips 202 defining an outer surface 203. In some examples, implantable medical electrical lead 200 may include a single bonding strip 202. In other examples, implantable medical electrical lead 200 may include more than two bonding strips 202. Bonding strips 202 includes a thermoplastic, such as, for example, a polyurethane-based polymer, polytetrafluoroethylene, ethylene tetrafluoroethylene, or other bio-stable thermoplastics. Bio-stable or bio-stability may include the characteristic of a material to remain chemically stable within the human body. In some implementations, bonding strips 202 and elongate lead body 204 may include the same material. In other implementations, bonding strips 202 and elongate lead body 204 may include different materials. The material of bonding strips 202 may be selected to become moldable or flow when heated to a selected temperature range and, optionally, compressed under a selected pressure range. In some examples, the desired temperature range may be between a minimum temperature at which the material of bonding strips 202 becomes moldable or flows to a maximum temperature at which any component of implantable medical electrical lead 200 may be negatively affected by, for example, burning, charring, oxidizing, or reduced polymer bio-stability. In some examples, the desired pressure range may by between a minimum pressure required for bonding strips 202 to conform with defibrillation electrode coil 212 and/or adhere to at least a portion of lead body 204 and a maximum pressure at which bonding strips 202 may flow beyond a desired region defined by bonding strips 202.

Bonding strips 202 extends substantially axially along defibrillation electrode coil 212 (e.g., parallel to or nearly parallel to the X-X axis). Bonding strips 202 may extend along at least a portion of defibrillation electrode 212. In examples in which bonding strips 202 include two or more bonding strips 202, each respective bonding strip of bonding strips 202 may be positioned along the same or different circumferential positions on elongate lead body 204 relative to the other bonding strips of bonding strips 202. The length ($L_A$ and $L_B$) of bonding strips 202 may be selected based on the length ($L_E$) of defibrillation electrode coil 212 to be bonded to elongate lead body 204. In some examples, length ($L_E$) of defibrillation electrode coil 212 may be between about 0.05 millimeters and about 20 centimeters, such as between about 0.1 millimeters and about 10 centimeters or between about 4 centimeters and about 8 centimeters. In some examples, the length ($L_A$ and $L_B$) of bonding strips 202 may be between about 0.05 millimeters and about 20 centimeters, such as between about 0.1 millimeters and about 10 centimeters or between about 4 centimeters and about 8 centimeters. In some examples, the length of bonding strips 202 (e.g., total length $L_A$ plus $L_B$) is approximately the same as the length ($L_E$) of defibrillation electrode coil 212.

As shown in FIGS. 2C and 2D, bonding strips 202B may include an integrally formed collar 218. In some examples, each respective bonding strip of bonding strips 202 may include one or more integrally formed collar 218 at one or both ends of each respective bonding strip of bonding strips 202, and/or at one or more positions between the ends of each respective bonding strip of bonding strips 202. Integrally formed collar 218 may extend circumferentially around the entire circumference of elongate lead body 204. Integrally formed collar 218 may include any suitable width (AO or any suitable thickness ($T_c$). In some examples, the width ($w_c$) and/or thickness ($T_c$) of integrally formed collar 218 may be the same as or similar to the width ($w_B$) and/or thickness (T) of bonding strips 202. Integrally formed collar 218 may be configured to encapsulate at least a portion of an electrical connection 222 between defibrillation electrode coil 212 and conductor 220. For example, conductor 220 may extend from lumen 206A, through elongate lead body 204 or a channel formed in elongate lead body 204 to electrical connection 222 on turn 210E of plurality of turns 210. By encapsulating electrical connection 222, collar 218 may improve the resilience of electrical connection 222.

In some examples, a thickness (T) of bonding strips 202 in a radial direction of implantable medical electrical lead 200 is greater than a diameter (D) of the filars of defibrillation electrode coil 212. By including a thickness of bonding strips 202 greater than a diameter of the filars of defibrillation electrode coil 212, bonding strips 202 may electrically insulate at least a portion of defibrillation electrode coil 212. In some examples, a thickness (T) of bonding strips 202 in a radial direction of implantable medical electrical lead 200 is between about 0.05 millimeters and about 0.5 millimeters, such as between about 0.1 millimeters and about 0.3 millimeters. In this way, bonding strips 202 may be used to control the directionality of the electrical stimulation therapy relative to implantable medical electrical lead 200. For example, during delivery of an electrical simulation therapy, current may travel from only exposed portions of defibrillation electrode coil 212 to another electrode (such as an electrode on the housing of ICD 110). Additionally, or alternatively, a thickness of bonding strips 202 greater than a diameter of the filars of defibrillation electrode coil 212 may provide a desired resilience to reduce damage to implantable medical electrical lead 200 during manufacturing, handling, or implantation of implantable medical electrical lead 200. For example, bonding strips 202 that are thicker than a diameter of the filars of defibrillation electrode coil 212 may have reduced cracking, breakage, or delamination from elongate lead body 204 than a thinner bonding strips 202. In some examples, a thickness (T) of bonding strips 202 in a radial direction of implantable medical electrical lead 200 is less than a diameter (D) of the filars of defibrillation electrode 212.

For at least some of the length of bonding strips 202, bonding strips 202 extends only partially around the circumference of defibrillation electrode coil 212. For example, as shown in FIG. 2B, the width of bonding strips 202 is about 20% of the circumference of elongate lead body 204. In other examples, bonding strips 202 may extend around between about 15% or about 85% of the circumference of elongate lead body 204.

The width ($w_B$) of bonding strips 202 relative to the circumference of elongate lead body 204 (and, thus, defibrillation electrode coil 212) may affect a conductance of defibrillation electrode coil 212. For example, the portion of defibrillation electrode coil 212 covered by bonding strips 202 may be electrically insulated, e.g., from the surrounding tissue of a patient. Generally, conductance, G, is approximately equal to $G = \sigma \cdot A/l$, where $\sigma$ is the electrical conductivity of the conductor, A is the cross-sectional area of the conductor, and l is the length of the conductor. In examples in which defibrillation electrode coil 212 is positioned in a patient to conduct electrical simulation through a ventricle of the heart, conductance may be proportional to the conductive surface area (e.g., exposed surface area) of defibrillation electrode coil 212. By selecting a width of bonding strips 202 on defibrillation electrode coil 212, the conductance of defibrillation electrode coil 212 may be controlled. In this way, a width of bonding strips 202 may be selected to enable an IMD system to provide sufficient current for extravenous electrotherapy and enough resilience of defibrillation electrode coil 212 to reduce damage to implantable medical electrical lead 200 during manufacturing, handling, or implantation of implantable medical electrical lead 200.

Similarly, a conductance of defibrillation electrode coil 212 is associated with the length of bonding strips 202. For example, a length of bonding strips 202 may be selected to enable an IMD system to provide sufficient current for electrical stimulation therapy and enough resilience of defibrillation electrode coil 212 to reduce damage to implantable medical electrical lead 200 during manufacturing, handling, or implantation of implantable medical electrical lead 200.

In some examples, outer surface 203 of bonding strips 202 is substantially planar. In other examples, outer surface 203 may be non-planar. For example, the thickness of bonding strips 202 may be substantially constant and outer surface 203 may substantially follow contours defined by adjacent turns of plurality of turns 210 and portions of elongate lead body 204 between adjacent turns of plurality of turn 210. In some examples, one or both ends of a respective bonding strip of bonding strips 202 (e.g., collar 218) may be tapered to provide a smooth transition from elongate lead body 204 to defibrillation electrode coil 212. In some examples, outer surface 203 may be at least partially discontinuous. For example, at least a portion of turns of plurality of turns 210 may protrude through outer surface 203. In this way, bonding strips 202 may encapsulate at least a portion of each of plurality of turns 210 of at least one filar of defibrillation electrode coil 212.

At least a portion 214 of bonding strips 202 is bonded to elongate lead body 204. In some examples, the bond at portion 214 does not include an adhesive. For example, portion 214 of bonding strips 202 may be thermally bonded to elongate lead body 204. In some examples, bonding strips 202 may encapsulate at least a portion of each of plurality of turns 210 of at least one filar of defibrillation electrode coil 212 to fill some or substantially all of the space between each adjacent pair of turns of plurality of turns 210 and surface 205 of elongate lead body 204. For example, an air gap 216 may be present between adjacent filars of defibrillation electrode 212. In this way, bonding strips 202 may fix a portion (e.g., each adjacent pair of turns of plurality of turns 210) of defibrillation electrode coil 212 to elongate lead body 204.

In some examples, elongate lead body 204 defines a substantially serpentine shape including at least one bend. In some examples, the serpentine shape of elongate lead body 204 may be selected to control the electric field generated by the defibrillation pulses, for example, to increase the surface area of the exposed surface of defibrillation electrode coil 212 that is proximal to the heart of a patient. In examples in which elongate lead body 204 defines a substantially serpentine shape, bonding strips 202 may be disposed on a surface of elongate lead body 204 perpendicular to the at least one bend. In this way, bonding strips 202 may be positioned on a surface of elongate lead body 204 opposite the heart of the patient. By positioning bonding strips 202 on a surface of elongate lead body 204 opposite the heart of the patient, bonding strips 202 may help direct electrical simulation toward the heart. In other words, bonding strips 202 may insulate defibrillation electrode coil 212 from tissue of the patient that does not form the therapy vector.

In some examples, implantable medical electrical lead 200 may include a second defibrillation electrode (e.g., defibrillation electrodes 106A and 106B of FIG. 1A) positioned along the distal portion of elongate lead body 204 distal to defibrillation electrode 208. The second defibrillation electrode may be substantially similar to defibrillation electrode 208. For example, second defibrillation electrode may include a second defibrillation electrode coil bonded to elongate lead body 204 by a second bonding strip extending axially along the second defibrillation electrode coil and extending only partially around the circumference of the second defibrillation electrode coil. In some examples, defibrillation electrode coil 212 and the second defibrillation electrode coil may be spaced apart by about 1 millimeter to about 3 centimeters, or about 0.5 centimeters to about 2 centimeters. In some examples, the second defibrillation electrode coil may enable implantable medical electrical lead 200 of an IMD system to use multiple therapy vectors to improve directionality and/or magnitude of an electrical simulation therapy. In some examples, defibrillation electrode coil 212 and the second defibrillation electrode coil may define a common electrode in a therapy vector. For example, defibrillation electrode coil 212 and the second defibrillation electrode coil may define the cathode or anode and the ICD may define or include the other of the cathode or anode to define a therapy vector extending from the defibrillation electrode coil 212 and the second defibrillation electrode coil to the ICD. In some examples, defibrillation electrode coil 212 may define the cathode or anode and the second defibrillation electrode coil may define the other of the cathode or anode to define a therapy vector extending from the defibrillation electrode coil 212 to the second defibrillation electrode coil.

Figure 3:
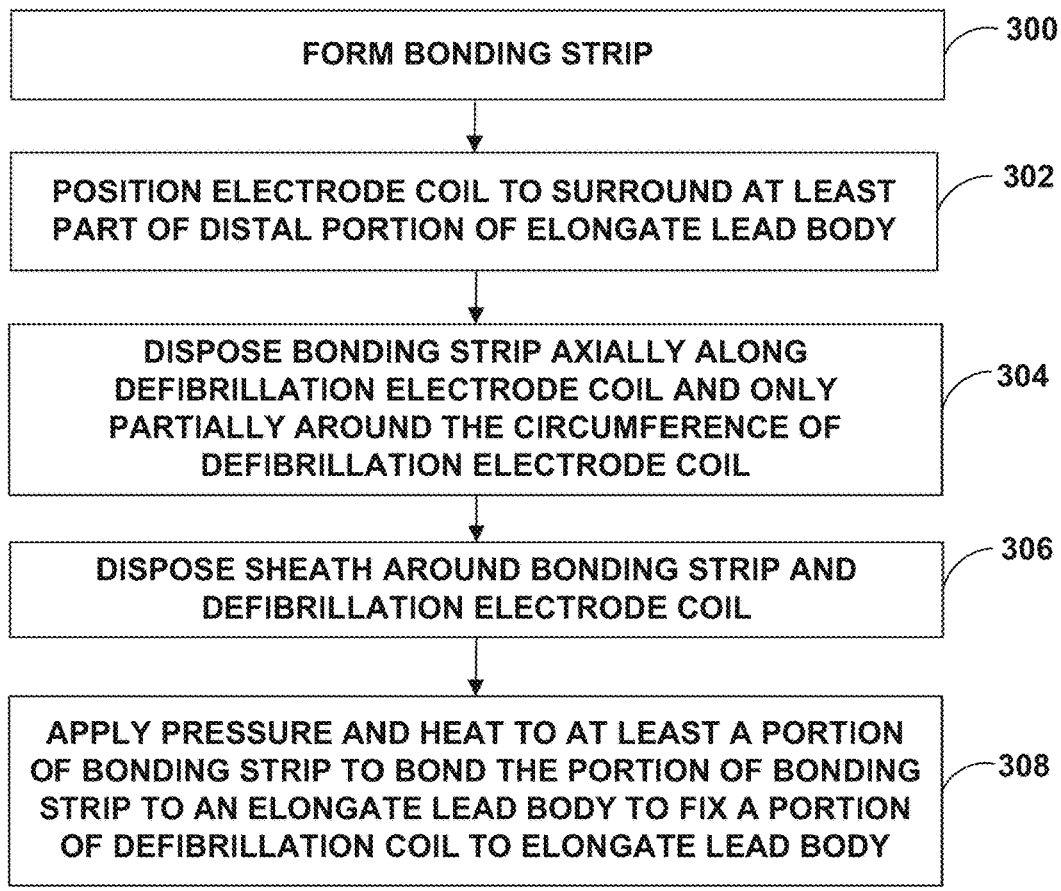
FIG. 3 is a flow diagram illustrating an example technique for forming a medical electrical lead.

Implantable medical electrical lead 200 may be formed using any suitable technique. FIG. 3 is a flow diagram illustrating an example technique for forming a medical electrical lead. The technique of FIG. 3 will be described with reference to IMD system 100 of FIG. 1 and implantable medical electrical lead 200 of FIG. 2, although a person or ordinary skill in the art will appreciate that similar techniques may be used to form the same or similar IMD systems or medical electrical leads.

The technique of FIG. 3 optionally includes forming bonding strips 202 (300). For example, forming bonding strips 202 may include cutting (e.g., mechanical cutting or laser cutting) bonding strips 202 having a selected length, a selected width, and a selected shape from a sheet of material. The thickness of the sheet of material may be a desired thickness, e.g., greater than a diameter of the at least one filar. In other examples, forming bonding strips 202 may include cutting bonding strips 202 to a desired thickness. Forming bonding strips 202 may optionally include defining one or more integrally formed collars 218, such that collars 218 are integrally formed at one or both ends of bonding strips 202. As discussed above, the length, width, and thickness of bonding strips 202 affect a conductance of defibrillation coil 212 and resilience of implantable medical electrical lead 200. In this way, forming bonding strips 202 may include selecting dimensions of bonding strips 202 to allow an IMD system to provide sufficient current for electrical stimulation therapy and while providing sufficient resilience to implantable medical electrical lead 200 to reduce damage to defibrillation coil 212 during manufacturing, handling, or implantation of implantable medical electrical lead 200.

The technique of FIG. 3 includes positioning an electrode coil to surround at least part of a distal portion of an elongate lead body extending from a proximal end to a distal end (302). As discussed above, defibrillation electrode coil 212 surrounds at least part of distal portion 114 of elongated lead body 102 extending from proximal end 112 to distal end 114. In some examples, positioning the electrode coil may include positioning a plurality of electrode coils 106 and/or positioning one or more sensing and/or pacing electrodes 108.

The technique of FIG. 3 includes disposing bonding strips 202 axially along defibrillation electrode coil 212 and only partially around the circumference of defibrillation electrode coil 212 (304). In some examples, disposing bonding strips 202 axially along defibrillation electrode coil 212 and only partially around the circumference of defibrillation electrode coil 212 (304) may include temporarily fixing bonding strips 202 to defibrillation electrode coil 212 with an adhesive or retainer, such as a plastic clip or elastic band.

The technique of FIG. 3 optionally includes, after disposing bonding strips 202 on defibrillation electrode coil 212, disposing a sheath around bonding strips 202 and defibrillation electrode coil 212 (306). The sheath material may be selected to reduce bonding (e.g., thermal bonding) of the sheath to bonding strips 202, defibrillation electrode coil 212, and elongate lead body 204. In some examples, the sheath may include a silicone-based material. The sheath may be configured to reduce a potential of damage to implantable medical electrical lead 200 during subsequent heating and/or pressure treatment to bond bonding strips 202 to elongate lead body 204. By surrounding bonding strips 202 and defibrillation electrode coil 212 with the sheath (306), heat and/or pressure may be applied directly to the sheath and indirectly to bonding strips 202 or other portions of implantable medical electrical lead 200.

The technique of FIG. 3 also includes, after disposing bonding strips 202 on defibrillation electrode coil 212, applying pressure and heat to at least a portion of bonding strips 202 to bond the portion of bonding strips 202 to elongate lead body 204 to fix a portion of defibrillation electrode coil 212 to elongate lead body 204 (308). Pressure may be applied by any suitable means. For example, actuation (e.g., mechanical, pneumatic, or the like) of a die or similar structure may directly or indirectly apply pressure to at least a portion of bonding strips 202. Heat may be applied by any suitable means, such as, for example, conduction, convention, or radiation. For example, conduction heat may be applied directed or indirectly to bonding strips 202 via a heated metal die. In this way, bonding strips 202 may be thermally bonded to at least a portion of elongate lead body 204. After bonding the portion of bonding strips 202 to elongate lead body 204, bonding strips 202 may encapsulate at least a portion of each turn of plurality of turns 210 of at least one filar of defibrillation electrode coil 212. By encapsulating at least a portion of each turn of plurality of turns 210 of at least one filar of defibrillation electrode coil 212, bonding strips 202 may affect a conductance of defibrillation electrode coil 212, as discussed above.

The technique of FIG. 3 optionally includes, after bonding the portion of the bonding strips 202 to elongate lead body 204, thermoforming implantable medical electrical lead 200 (e.g., elongate lead body 204) to define a substantially serpentine shape that includes at least one bend. In some examples, bonding strip 212 may be disposed on a surface of elongate lead body 204 perpendicular to the at least one bend. By positioning bonding strips 202 on a surface perpendicular to the at least one bend, implantable medical electrical lead 200 may be positioned in a patient with bonding strips 202 distal to the heart of the patient (e.g., an exposed portion of defibrillation electrode coil 212 proximal of the heart of the patient). By positioning bonding strips 202 distal to the heart of the patient, bonding strips 202 may direct an electrical simulation toward the heart. For example, bonding strips 202 may insulate defibrillation electrode coil 212 from tissue of the patient that does not form the therapy vector. In this way, bonding strips 202 may control a directionality of an electrical simulation therapy.

The technique of FIG. 3, including any or all of the described optional steps, may be applied to any number of defibrillation electrode coils for a single lead. For example, if an implantable medical electrical lead 200 includes two defibrillation electrode coils, a respective bonding strip may be disposed over the respective defibrillation electrode coil and bonded to elongate lead body 204.

Figure 4:
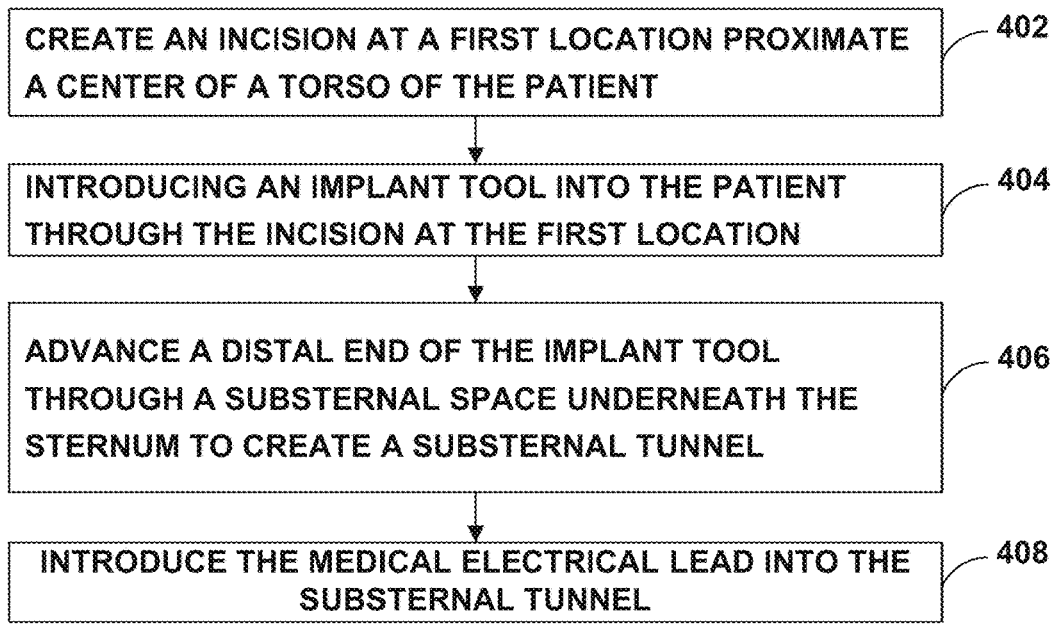
FIG. 4 is a flow diagram illustrating an example technique for implanting in a patient a medical electrical lead.

As discussed above, bonding strips 202 may reduce damage to implantable medical electrical lead 200 during implantation of implantable medical electrical lead. FIG. 4 is a flow diagram illustrating an example technique of implanting in a patient an implantable medical electrical lead. The technique of FIG. 4 will be described with reference to IMD system 100 of FIG. 1 and implantable medical electrical lead 200 of FIG. 2, although a person or ordinary skill in the art will appreciate that similar techniques may be used to implant the same or similar IMD systems or implantable medical electrical leads. Additionally, a person or ordinary skill in the art will appreciate that IMD system 100 or implantable medical electrical lead 200 may be implanted using different implantation techniques.

The technique illustrated in FIG. 4 includes creating an incision at a first location proximate a center of a torso (e.g., proximate to the xiphoid process) of the patient (402), introducing an implant tool into the patient through the incision at the first location (404), advancing a distal end of the implant tool through a substernal space underneath the sternum to create a substernal tunnel (406), and introducing implantable medical electrical lead 200 into the substernal tunnel such that the distal portion of elongate lead body 204 (e.g., defibrillation electrode coil 212) is positioned in a desired location (408). In some examples, the desired location may be between a first position proximate to the xiphoid process and a second position superior to the xiphoid process such that the defibrillation electrode coil is positioned anterior to a right ventricle of the heart and the bonding strip is positioned anterior to the defibrillation electrode coil. In some examples, the technique illustrated in FIG. 4 includes retracting the implant tool.

In some examples, introducing implantable medical electrical lead 200 into the substernal tunnel may include temporarily deforming implantable medical electrical lead 200. For example, implantable medical electrical lead 200 including a serpentine shape may be straightened as implantable medical electrical lead 200 is introduced to the tunnel. Straightening implantable medical electrical lead 200 may cause one or more respective turns of plurality of turns 210 to move relative to adjacent turns of plurality of turns 210, e.g., by bending, compressing, or twisting. In some examples, implantable medical electrical lead 200 may return to the serpentine shape as the implant tool or sheath associated with the implant tool is withdrawn. Bonding strips 202 contribute to flexibility of implantable medical electrical lead 200 and constrain movement of the plurality of turns 210 relative to each other. In this way, bonding strips 202 may improve the resilience of implantable medical electrical lead 200 to enable implantable medical electrical lead 200 to return to the serpentine shape and to reduce or eliminate damage to implantable medical electrical lead 200 due to excessive movement of plurality of turns 210 relative to each other.

EXAMPLES

Figure 5A:
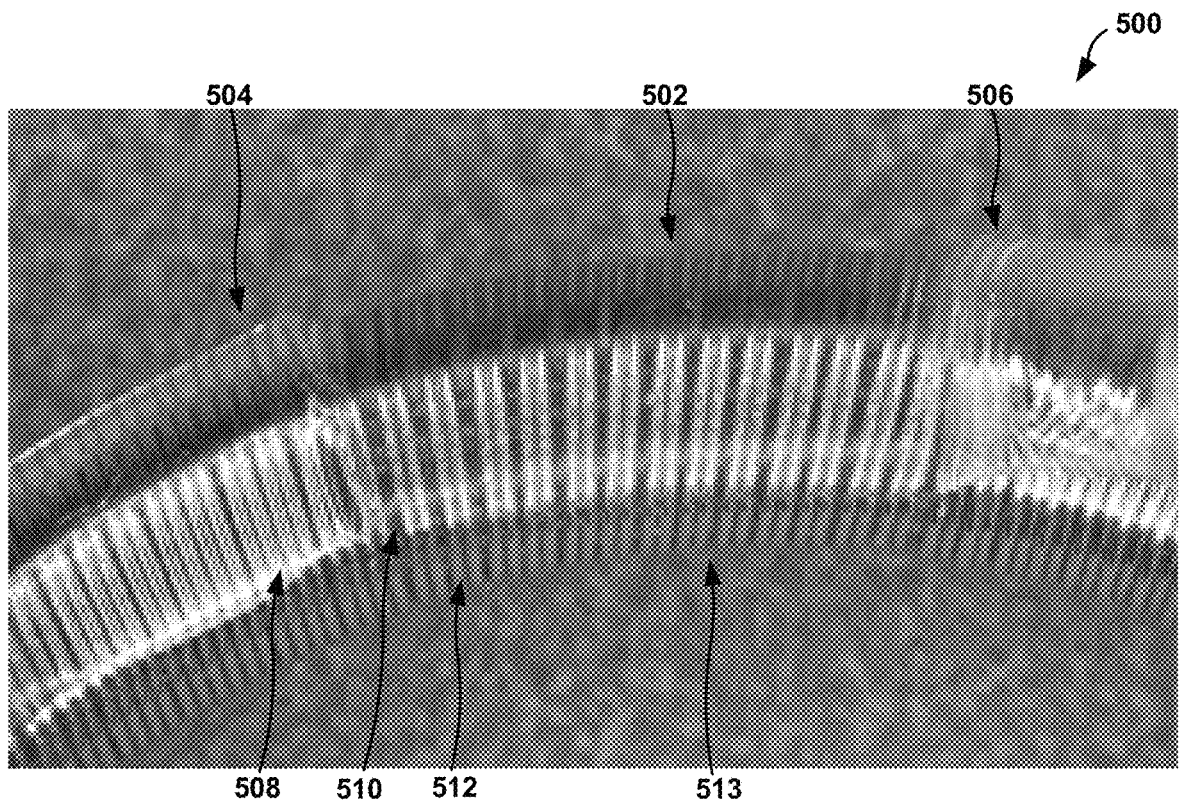
FIGS. 5A and 5B are photographs illustrating a portion of a medical electrical lead including an elongate lead body, an elongate electrode coil, and a bonding strip that is thermally bonded to the elongate lead body.
Figure 5B:
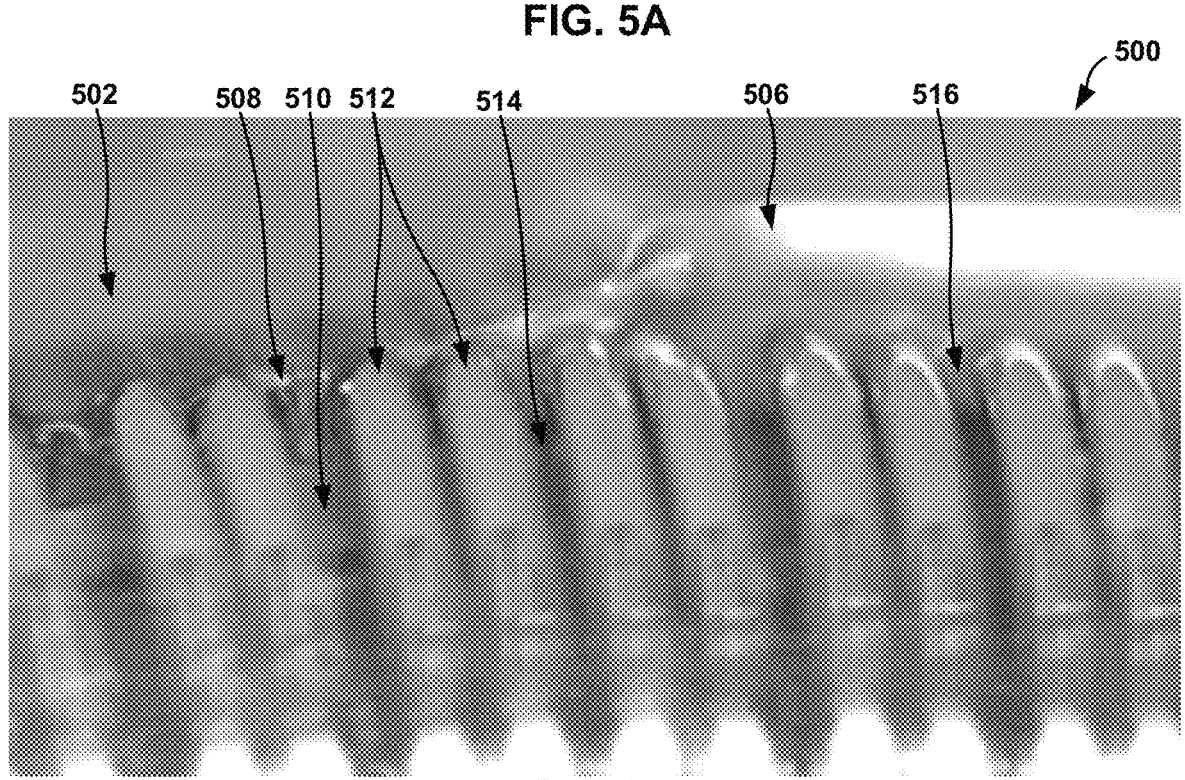

FIG. 5A is a photograph illustrating a portion of a medical electrical lead 500 including an elongate lead body 510, an electrode coil 512, and a bonding strip 508 that is thermally bonded to elongate lead body 510. FIG. 5B is a photograph illustrating a magnified view of a portion of FIG. 5A. Medical electrical lead 500 may be the same or substantially similar to implantable medical electrical lead 200 discussed above with respect to FIGS. 2A and 2B. For example, medical electrical lead 500 includes elongate lead body 510, an electrode coil 512, and a bonding strip 508.

As shown in FIG. 5A, medical electrical lead 500 includes bonding strip 508 having a bonded portion 502 and non-bonded portions 504 and 506. Bonding strip 508 extends only partially around the circumference of electrode coil 512, e.g., a portion 513 of electrode coil 512 is left exposed. Bonded portion 502 may include a thermal bond between bonding strip 508 and elongate lead body 510 at interface 514 between adjacent turns of electrode coil 512. Bonding strip 508 encapsulates at least a portion of electrode coil 512. While implantable medical electrical lead 500 includes nonbonded portions 504 and 506, nonbonded portions 504 and 506 are shown for illustration purposes. For example, bonded portion 502 may be formed by a first bonding procedure, e.g., as discussed above with respect to FIG. 3. Nonbonded portions 504 and 506 may be subsequently bonded by subsequent bonding procedures. In some examples, nonbonded portions 504 and 506 may include a plurality of air gaps (e.g., air gap 516) between bonding strip 508 and elongate lead body 510.

Various examples have been described. These and other examples are within the scope of the following claims.

What is claimed is:
1. A medical electrical lead comprising:
an elongate lead body extending axially from a proximal end to a distal end and comprising a proximal portion and a distal portion;
an elongate electrode coil circumferentially surrounding at least part of the distal portion of the elongate lead body; and
a bonding strip extending continuously in an axial direction along the elongate lead body and the elongate electrode coil, wherein a width of the bonding strip extends only partially around a circumference of the elongate lead body for at least part of a length of the bonding strip, wherein at least the part of the length of the bonding strip is bonded to the elongate lead body to fix a portion of the elongate electrode coil to the elongate lead body.
2. The medical electrical lead of claim 1, wherein the elongate electrode coil comprises a plurality of turns of at least one filar, wherein the bonding strip encapsulates at least a portion of the plurality of turns.
3. The medical electrical lead of claim 1, wherein the width of the bonding strip is selected to affect a conductance of the elongate electrode coil.

4. The medical electrical lead of claim 1, wherein the elongate electrode coil comprises at least one filar, wherein a thickness of the bonding strip in a radial direction of the medical electrical lead is greater than a diameter of the at least one filar.
5. The medical electrical lead of claim 1, wherein the elongate lead body defines a substantially serpentine shape comprising at least one bend, wherein the bonding strip is disposed on a surface of the elongate lead body perpendicular to the at least one bend.
6. The medical electrical lead of claim 1, wherein the bonding strip comprises a thermoplastic.
7. The medical electrical lead of claim 1, wherein the elongate lead body and the bonding strip each comprise a polyurethane-based polymer.
8. The medical electrical lead of claim 1, wherein the portion of the bonding strip is thermally bonded to the portion of the elongate lead body.
9. The medical electrical lead of claim 1, wherein the bonding strip further comprises an integrally formed collar at one or both ends of the bonding strip.
10. The medical electrical lead of claim 9, wherein the collar extends circumferentially around the entire circumference of the elongate lead body.
11. The medical electrical lead of claim 9, wherein the elongate electrode coil is electrically coupled to a conductor at an electrical connection, and wherein the collar is configured to encapsulate at least a portion of the electrical connection.
12. The medical electrical lead of claim 11, wherein the elongate lead body further comprises a lumen, and wherein the conductor is disposed in the lumen.
13. The medical electrical lead of claim 1, wherein a length of the bonding strip is approximately the same as a length of the elongate electrode coil.
14. The medical electrical lead of claim 1, further comprising:
a second elongate electrode coil positioned along the distal end of the elongate lead body distal to the elongate electrode coil; and
a second bonding strip extending axially along the second elongate electrode coil and extending only partially around a circumference of the second elongate electrode coil, wherein the second bonding strip is bonded to the elongate lead body to fix a portion of the second elongate electrode coil to the elongate lead body.
15. A method for implanting a medical electrical lead that includes an elongate lead body extending axially from a proximal end to a distal end and comprising a proximal portion and a distal portion, an elongate electrode coil circumferentially surrounding at least part of the distal portion of the elongate lead body, and a bonding strip extending continuously in an axial direction along the elongate lead body and the elongate electrode coil, wherein a width of the bonding strip extends only partially around a circumference of the elongate lead body for at least part of a length of the bonding strip, wherein at least the part of the length of the bonding strip is bonded to the elongate lead body to fix a portion of the elongate electrode coil to the elongate lead body, the method comprising:
creating an incision at a first location proximate a center of a torso of a patient;
introducing an implant tool into the patient through the incision at the first location;
advancing a distal end of the implant tool through a substernal space underneath the sternum to create a substernal tunnel;

introducing the medical electrical lead into the substernal tunnel such that the distal portion of the elongate lead body is positioned between a first position proximate to the xiphoid process and a second position superior to the xiphoid process such that the elongate electrode coil is positioned anterior to a right ventricle of the heart and the bonding strip is positioned anterior to the elongate electrode coil.

16. A method of forming a medical electrical lead comprising:
    positioning an elongate electrode coil to circumferentially surround at least part of a distal portion of an elongate lead body extending axially from a proximal end to a distal end;
    disposing an axially continuous bonding strip along the elongate lead body and the elongate electrode coil, wherein a width of the bonding strip extends only partially around a circumference of the elongate lead body for at least part of a length of the bonding strip; and
    applying pressure and heat to at least the part of the length of the bonding strip to bond the part of the length of the bonding strip to the elongate lead body to fix a portion of the elongate electrode coil to the elongate lead body.

17. The method of claim 16, further comprising, after disposing the bonding strip, surrounding at least the portion of the bonding strip and the elongate lead body with a silicone-based sheath, wherein applying pressure and heat to the portion of the bonding strip comprises applying pressure and heat to the silicone-based sheath.

18. The method of claim 16, wherein applying pressure and heat to the portion of the bonding strip comprises compressing the portion of the bonding strip in a heated metal die.

19. The method of claim 16, wherein, after bonding the portion of the bonding strip to the elongate lead body, the bonding strip encapsulates at least a portion of each of a plurality of turns of at least one filar of the elongate electrode coil.

20. The method of claim 16, wherein, after bonding the portion of the bonding strip to the elongate lead body, a conductance of the elongate electrode coil is associated with the width of the bonding strip.

21. The method of claim 16, wherein the elongate electrode coil comprises at least one filar, wherein a thickness of the bonding strip in a radial direction of the medical electrical lead is greater than a diameter of the at least one filar.

22. The method of claim 16, further comprising, after bonding the portion of the bonding strip to the elongate lead body, thermoforming the elongate lead body to define a substantially serpentine shape comprising at least one bend, wherein the bonding strip is disposed on a surface of the elongate lead body perpendicular to the at least one bend.

23. The method of claim 16, wherein the bonding strip comprises a thermoplastic.

24. The method of claim 16, wherein the bonding strip comprises a polyurethane-based polymer.

25. The method of claim 16, wherein the portion of the bonding strip is thermally bonded to the portion of the elongate lead body.

26. The method of claim 16, wherein applying pressure and heat to the portion of the bonding strip comprises applying pressure and heat to an integrally formed collar at one or both ends of the bonding strip.

27. The method of claim 26, wherein the integrally formed collar extends circumferentially around the entire circumference of the elongate lead body.

28. The method of claim 26, wherein positioning the elongate electrode coil comprises electrically coupling the elongate electrode coil to a conductor at an electrical connection, and wherein disposing the bonding strip comprises positioning the integrally formed collar to encapsulate at least a portion of the electrical connection.

29. The method of claim 16, wherein a length of the bonding strip is approximately the same as a length of the elongate electrode coil.

30. The method of claim 16, further comprising, after disposing the bonding strip,
    disposing a second bonding strip axially along a second elongate electrode coil and only partially around a circumference of the second elongate electrode coil, wherein the second elongate electrode coil surrounds at least part of the distal portion of the elongated lead body distal to the elongate electrode coil,
    wherein applying pressure and heat further comprises applying pressure and heat to at least a portion of the second bonding strip to bond the portion of the second bonding strip to the elongate lead body to fix a portion of the second elongate electrode coil to the elongate lead body.

* * * * *